United States Patent
Torrie

(10) Patent No.: US 10,245,045 B2
(45) Date of Patent: Apr. 2, 2019

(54) RESECTION INSTRUMENT

(75) Inventor: Paul Alexander Torrie, Marlborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/173,801

(22) Filed: Jun. 30, 2011

(65) Prior Publication Data

US 2012/0004662 A1  Jan. 5, 2012

Related U.S. Application Data

(60) Provisional application No. 61/359,855, filed on Jun. 30, 2010.

(51) Int. Cl.
| | | |
|---|---|---|
| *A61B 17/56* | (2006.01) | |
| *A61B 17/17* | (2006.01) | |
| *A61B 17/16* | (2006.01) | |

(52) U.S. Cl.
CPC ...... *A61B 17/1742* (2013.01); *A61B 17/1666* (2013.01); *A61B 17/1662* (2013.01); *A61B 2017/1602* (2013.01)

(58) Field of Classification Search
CPC ............ A61B 17/1664; A61B 17/1666; A61B 17/1742; A61B 17/1746; A61B 2017/1602; A61B 17/1677; A61B 17/1675; A61B 17/1659
USPC ...... 606/79, 80, 86 R–90, 102, 160; 30/43.4, 30/43.5, 529, 2; 132/76.4
See application file for complete search history.

(56) References Cited

U.S. PATENT DOCUMENTS

| | | | |
|---|---|---|---|
| 1,722,748 A | | 7/1929 | Holden, Jr. |
| 2,173,751 A | * | 9/1939 | Burkhart ................. A01F 11/06 30/121.5 |
| 3,776,649 A | * | 12/1973 | Kemezys ........................ 403/90 |
| 3,797,505 A | * | 3/1974 | Gilhaus ................ A61B 17/322 132/76.4 |
| 4,208,791 A | * | 6/1980 | Van Cleve .............. B26B 21/18 30/346.58 |
| 4,528,980 A | | 7/1985 | Kenna |
| 5,269,785 A | | 12/1993 | Bonutti |
| 5,339,799 A | * | 8/1994 | Kami et al. ................... 600/117 |
| 6,022,362 A | * | 2/2000 | Lee et al. ...................... 606/159 |

(Continued)

FOREIGN PATENT DOCUMENTS

| | | |
|---|---|---|
| DE | 29814889 U1 | 12/1999 |
| EP | 0337901 A1 | 10/1989 |

(Continued)

OTHER PUBLICATIONS

International Search Report and Written Opinion for International Patent Application PCT/US2011/042676 dated Oct. 28, 2011.

(Continued)

*Primary Examiner* — Eric S Gibson
*Assistant Examiner* — Marcela I Shirsat
(74) *Attorney, Agent, or Firm* — Burns & Levinson, LLP; Joseph M. Maraia

(57) ABSTRACT

The present invention concerns a surgical instrument. There is described a surgical instrument including a shaft having a handle towards a proximal end, a template towards a distal end, and resecting means for removing tissue. The template is shaped to complement the contours of a joint surface.

42 Claims, 6 Drawing Sheets

(56) References Cited

U.S. PATENT DOCUMENTS

| | | | |
|---|---|---|---|
| 6,146,395 A * | 11/2000 | Kanz et al. | 606/159 |
| 6,231,611 B1 | 5/2001 | Mosseri | |
| 6,375,684 B1 | 4/2002 | Kriek | |
| 6,622,731 B2 | 9/2003 | Daniel et al. | |
| 6,632,233 B1 * | 10/2003 | Burgard | 606/169 |
| 7,516,672 B2 * | 4/2009 | Schroll | 73/756 |
| 2001/0012967 A1 * | 8/2001 | Mosseri | 623/23.12 |
| 2002/0072474 A1 | 6/2002 | Truckai | |
| 2003/0130741 A1 | 7/2003 | McMinn | |
| 2005/0060039 A1 | 3/2005 | Cyprien | |
| 2005/0197661 A1 * | 9/2005 | Carrison et al. | 606/79 |
| 2006/0004369 A1 * | 1/2006 | Patel et al. | 606/79 |
| 2006/0079963 A1 | 4/2006 | Hansen | |
| 2006/0084368 A1 * | 4/2006 | Kapgan | B23B 51/101 451/51 |
| 2006/0100632 A1 * | 5/2006 | Fell | 606/81 |
| 2006/0111722 A1 * | 5/2006 | Bouadi | A61B 17/1604 606/79 |
| 2007/0118135 A1 * | 5/2007 | Mansmann | 606/80 |
| 2007/0288029 A1 | 12/2007 | Justin et al. | |
| 2009/0012526 A1 | 1/2009 | Fletcher | |
| 2009/0281545 A1 | 11/2009 | Stubbs | |
| 2010/0049200 A1 | 2/2010 | Re | |
| 2011/0270256 A1 | 11/2011 | Nelson et al. | |
| 2012/0046526 A1 * | 2/2012 | Boettner | A61B 17/025 600/210 |

FOREIGN PATENT DOCUMENTS

| | | |
|---|---|---|
| EP | 1669034 A1 | 6/2006 |
| FR | 319465 | 3/1902 |
| FR | 2833478 A1 | 6/2003 |
| JP | H0661215 U | 8/1994 |
| WO | WO2010033473 A2 * | 3/2010 |

OTHER PUBLICATIONS

International Search Report for International Patent Application PCT/US2011/042672 dated Nov. 8, 2011.

Written Opinion for International Patent Application PCT/US2011/042672 dated Dec. 31, 2012.

International Search Report for International Patent Application PCT/US2011/042676 dated Oct. 28, 2011.

Written Opinion for International Patent Application PCT/US2011/042676 dated Dec. 31, 2012.

* cited by examiner

RESECTION INSTRUMENT

The present invention concerns a surgical instrument. In particular, the present invention relates to an instrument for resecting tissue.

In many joints, and in particular the hip joint, when the bones forming the joint are operated at the extremes in their range of motion, interference can occur between the bones. In the hip, for example, when the femur is flexed upwards it may collide with the rim of the socket or acetabulum, of the pelvis. When this occurs, any soft tissue which is caught between the colliding bones may be damaged and cause pain. The soft tissue that is caught is usually the labrum, which is a ring-like structure formed from cartilage that surrounds the acetabular rim.

The cartilage tissue is generally damaged as a result of the high sheer forces that the joint is subjected to through movement at the extreme limits in its mobility. This is particularly damaging to the patient because the cartilage acts as a buffer between adjacent bone surfaces of joints and provides the sliding surfaces which allow the joint to move fluidly. This helps to prevent wear and tear on the joint by stopping the bones of the joint from directly grinding against one another.

Cartilage tissue only has a very limited capacity for repair as it does not contain any blood vessels, and so where damage has occurred the growth of new tissue is extremely slow, if at all.

Interference in the hip joint can be eliminated by removing any bone tissue which interferes with movement of the joint. Typically, interference occurs from naturally occurring irregularities, known as Cam lesions or femoral neck bumps, on the otherwise generally spherical head of the femur. These are commonly removed by surgeons during open hip surgery. During the procedure the surgeon will utilise a generally spherical template by placing it over the generally spherical head of the femur, and then sliding the template around the femoral head until any gaps that occur between the template and the femoral head are observed. These gaps indicate a change in curvature, and any discrepancies or bumps can then be removed by, for example, a chisel or powered burr, to allow the joint to move without impedance.

Whereas, in the current arthroscopic approach, the surgeon must make an educated guess of where the "bump" is. Due to distortion of the arthroscopic image in the joint during the procedure, the awkward direction of view of the arthroscope used in hip and the difficulty of interoperatively moving the femur through its full range of motion, it is a clinical challenge to arthroscopically determine where and how much bone should be removed. Typically, a surgeon will remove some of the bump and then flex the hip to see if the joint is still impeded. This is difficult and often impractical as the arthroscopic view becomes occluded by soft tissue with this motion.

A more convenient arthroscopic approach could have considerable advantages over open surgical procedures if these obstacles were overcome. In particular, it would lead to a quicker rehabilitation with less chance for iatrogenic damage when dislocating the joint. Accordingly, there exists a need for a fully integrated arthroscopic approach.

The present invention seeks to overcome the above issues by providing a surgical instrument which can be used arthroscopically to remove a bone growth or irregularity in the surface of a bone, and any overlying cartilage tissue.

According to the present invention there is provided a surgical instrument comprising a shaft having a handle towards a proximal end, a template towards a distal end, and resecting means for removing tissue, wherein the template is shaped to complement the contours of a joint surface.

Preferably, the tissue is formed of cartilage or bone.

Preferably, the joint is the hip or ankle joint.

Suitably, the template is connected or coupled to, or formed at the distal end of the shaft by a resiliently flexible member. Suitably, the resiliently flexible member is configured to bias the template towards the tissue surface. Suitably, the resiliently flexible member comprises a Nitinol wire, a Nitinol tube, a spring, a live-hinge or a corrugated portion.

Alternatively, the template is pivotally connected at the distal end of the shaft. Suitably, the template has proximal and distal ends and is pivotally connected to the shaft therebetween. Preferably, the template is pivotally connected at or towards its proximal end with the shaft. Preferably, the pivotal connection allows the template to pivot within a single plane. Optionally, the pivotal connection is a universal joint or a ball-and-socket joint. Suitably, the universal joint or a ball-and-socket joint includes a lock to restrict motion of the joint to a single plane.

The flexibility in the template, relative to the shaft, allows the template to accurately follow the contours of the tissue surface and enables changes in the curvature of the tissue surface to be resected.

In further alternative embodiments, the template is connected with and is substantially rigid relative to the shaft.

Suitably, the template includes a tissue engaging surface. Suitably, the tissue engaging surface is curved. Preferably, at least a portion of the template directly engages with the tissue surface which includes tissue to be resected. In alternative embodiments, the template engages with a tissue surface which is complementary to the tissue surface which includes tissue to be resected. In use, the tissue engaging surface of the template allows a surgeon to observe differences in the curvature of a tissue surface by monitoring any deviations in gaps which appear between the template and the tissue surface as the template is moved across the tissue surface.

Preferably, the resecting means is a burr. Preferably, the burr comprises a burr-head mounted on, or formed integrally with, a burr-shaft. Preferably, the burr-shaft is coaxial with, and rotatable within, the instrument shaft. In alternative embodiments, the burr-shaft is in part coaxial with, and rotatable within, the instrument shaft. In these embodiments, a section of the burr-shaft, towards its distal end, may be curved, and the proximal end of the burr-shaft is coaxial with, and rotatable within, the shaft of the instrument.

Preferably, the burr-head is spherical. In preferred embodiments, the pivotal connection between the template and burr is aligned with the centre of the burr-head. Preferably, the curved surface of the template and the surface of the burr-head are tangential. Suitably, the tangential arrangement between the template and burr-head may be offset slightly deeper or shallower to account for cartilage compressibility. Preferably, the burr-shaft includes a piston or dampener, and may also include centring means—all of which help to maintain the tangential arrangement between the template and burr-head as their relative positioning changes during movement of the instrument over a tissue surface.

Preferably, the surgical instrument comprises control means for the resecting means. The control means enable the resecting means to be selectively activated for a fixed period of time to minimize collateral damage to surrounding tissue. This is particularly advantageous because it means that tissue is only resected when the resecting means is physically activated by the surgeon. This provides a more accurate instrument and also allows the surgeon to identify differences in the curvature of a tissue surface and move the template back and forth over the region of difference, before deciding to resect the tissue. The tissue surface will only be affected when the surgeon activates the resecting means, so any damage to tissue will be highly selective.

Suitably, the control means include one or more sensors which energize the burr when a bone growth or irregularity in the surface of tissue or bone is detected. Suitably, the sensor is a pressure sensor. Alternatively, the burr is constantly energized so that the tissue irregularity is removed as soon as it is sensed and contacted by the burr-head.

Alternatively, the resecting means is a radio frequency electrode. In further alternative embodiments, the resecting means includes the combination of a radio frequency electrode, and a burr as described above. Preferably, the radio frequency electrode can be selectively energised to mark or resect a region of the tissue surface. Use of the instrument in conjunction with control means permit the radio frequency electrode to be selectively energised for a fixed period of time, to minimize damage of surrounding tissue. A particular advantage of radio frequency electrodes is that the tissue may be marked and observed prior to resection. As above, the tissue is only marked or resected when the electrode is activated. This means that these instruments are especially accurate.

Optionally, the resecting means may be activated by suitable sensing means, or through the application of pressure. For example, in instruments employing a radio frequency electrode, the electrode may be activated automatically when it comes into contact with a bump by the application of pressure on a sensor or the electrode. Thereby, the radio frequency electrode is only energized when a non-spherical condition is detected.

Alternatively, the radio frequency electrode is constantly energized so that tissue irregularity is removed as soon as it is contacted.

An advantage of an instrument having an integral resecting means is that it removes the intermediate step of marking the cartilage or bone tissue with a separate instrument prior to its resection, which requires the removal of the marking instrument and subsequent introduction of a resecting instrument into the surgical site. This helps to reduce the overall time required to carry out the procedure, and may help to speed up recovery times.

In embodiments where the resecting means comprises a radio frequency electrode and burr, any cartilage tissue overlying a bump may be marked in-situ, prior to its removal, or may be removed prior to resection of any bone with the burr. This arrangement is advantageous because it allows the surgeon to be selective in their approach to removing the bump. An initial use of the radio frequency electrode to resect the cartilage tissue provides the surgeon with an opportunity to review prior to the resection of any bone tissue.

Preferably, the instrument includes a biasing means to bias the template towards the tissue surface. Suitably, the biasing means is the instrument shaft. Alternatively, the biasing means is a rod, spring, live-hinge or dampener which is biased to extend the template distally. In embodiments in which the biasing means is a rod, the rod may include a spring or dampener. In use, the biasing means acts to abut the distal end of the template against the tissue surface upon which the instrument is being used. This has the effect that the tissue surface is more accurately tracked when the instrument is passed over it, so that differences in the curvature of, for example, the femoral head can be more accurately identified and resected.

Preferably, the instrument includes an obturator for supporting and protecting the template whilst the instrument is packaged and/or when the instrument is being introduced into a surgical site. Suitably, the obturator is a solid cylindrical member or a hollow tubular member. Preferably, the obturator is a tubular member coaxially mounted with the instrument shaft. Preferably, the obturator includes an opening at a distal end. Suitably, the obturator is internally mounted within the instrument shaft. Preferably, the obturator is slidably or rotatably mounted within the shaft and interlocks with the template such that it may be held rigidly. Alternatively, the obturator is removable.

Alternatively, the tubular member is an outer sheath, mounted on the outer surface of the instrument shaft. Preferably, the outer sheath at least partly surrounds a portion of the outer surface of the shaft. Suitably, the outer sheath is slidably mounted or rotatably mounted on the shaft, or is removable. In embodiments in which the outer sheath is rotatably mounted on the shaft, the rotatable movement arises from a thread and complementary groove arrangement—for example the outer surface of the shaft may include a helical thread.

Preferably, the surgical instrument includes a lock to prevent the obturator from impeding movement of the template when in a deployed position, and for locking the instrument in the template-stowed position for transit. The lock may be any suitable locking means, such as a twist-lock, button or catch.

Optionally, the template further comprises one or more bearings which assist movement of the template over a surface. Suitably, the template comprises two, three, four, five or six bearings. Preferably, the template comprises two bearings. Preferably, the bearings are located towards distal and proximal ends of the template. The provision of one or more bearings allow the template to move more easily over the tissue surface.

The current invention provides an arthroscopic instrument that uses the curved surfaces of a joint to guide a resection tool to remove an interfering bone bump. The instrument extends the curve of the existing anatomy, for example the curvature of the femoral head.

The above and other aspects of the invention will now be described with reference to the following drawings in which.

Figure 1:
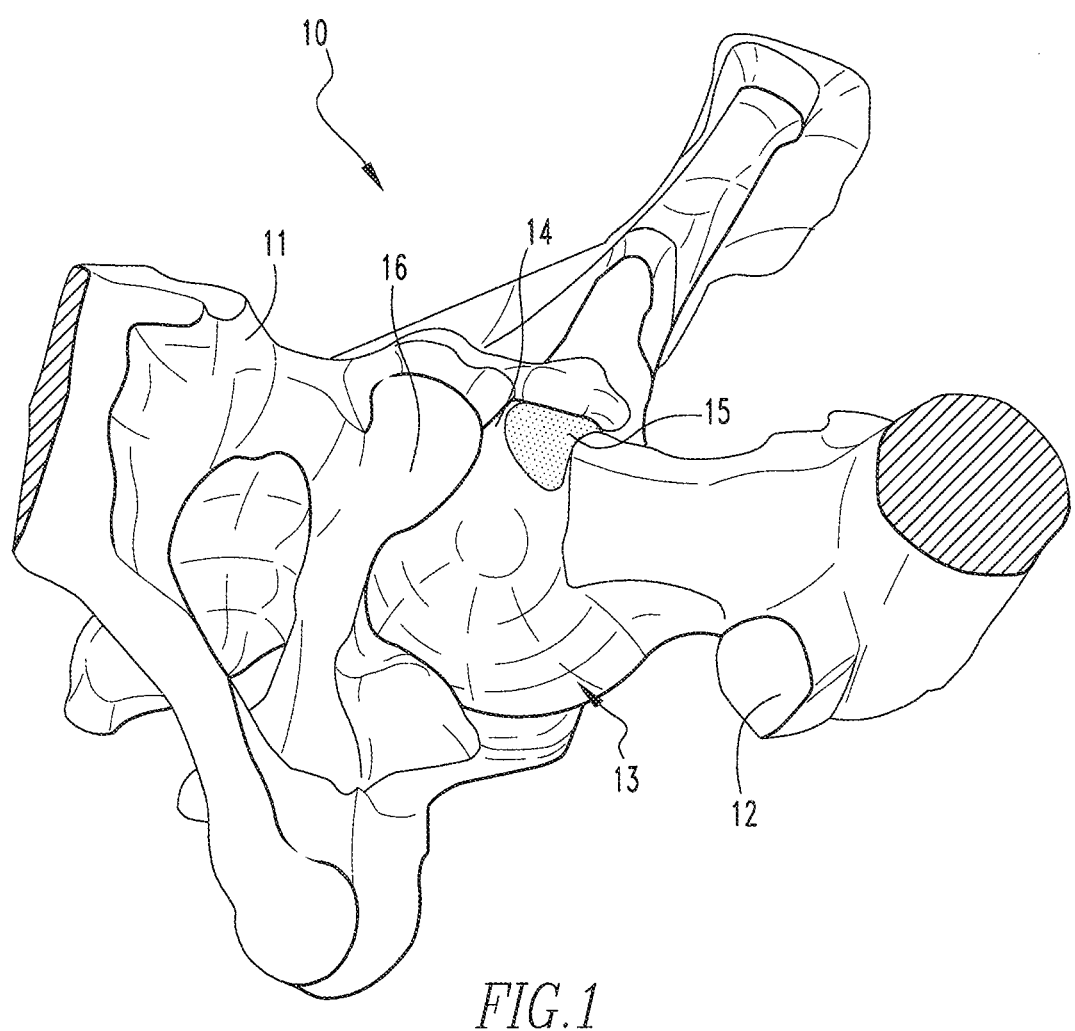
FIG. 1 is a partial view of a hip joint.

Referring to FIG. 1, there is shown a hip, or acetabulofemoral joint 10, formed from the femur 12 and acetabulum of the pelvis 11. Femur 12 includes a substantially spherical head 13, which locates in the cup-like acetabulum of the pelvis 11. The joint is lubricated with synovial fluid and its surfaces are lined with cartilage to cushion movement and allow it to move freely (not shown). The acetabulum is lined with the acetabular labrum, which is a ring-shaped fibrocartilaginous lip. The labrum extends beyond the acetabulum, forming a tight sliding connection with the femoral head and providing a stable joint.

The purpose of the hip joint is to support the weight of the body in both static and dynamic postures. Huge loads are placed upon the hip joint and any restrictions within the joint, such as bumps, can lead to significant damage to the surfaces of the joint over time.

Figure 2:
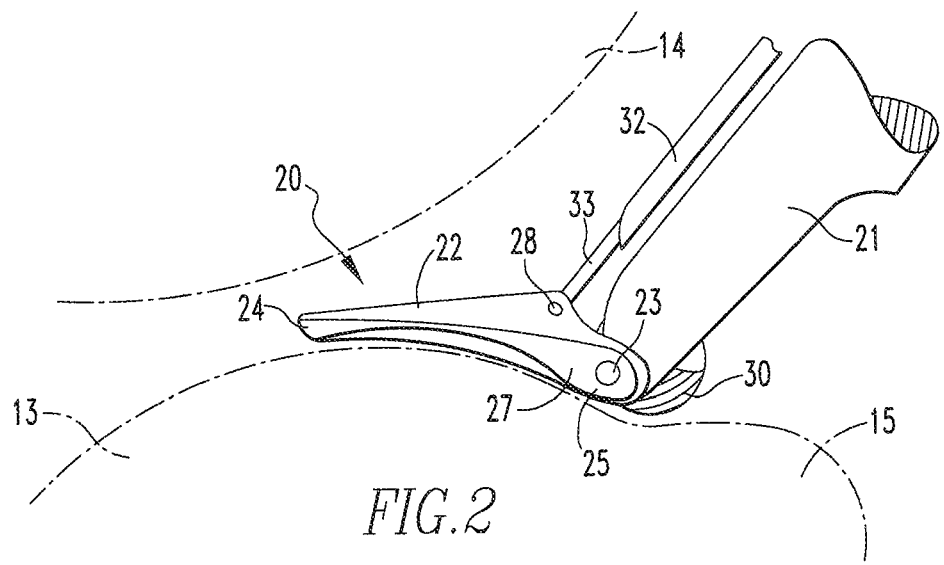
FIG. 2 is a schematic side view of a first embodiment of an instrument according to the invention.
Figure 3:
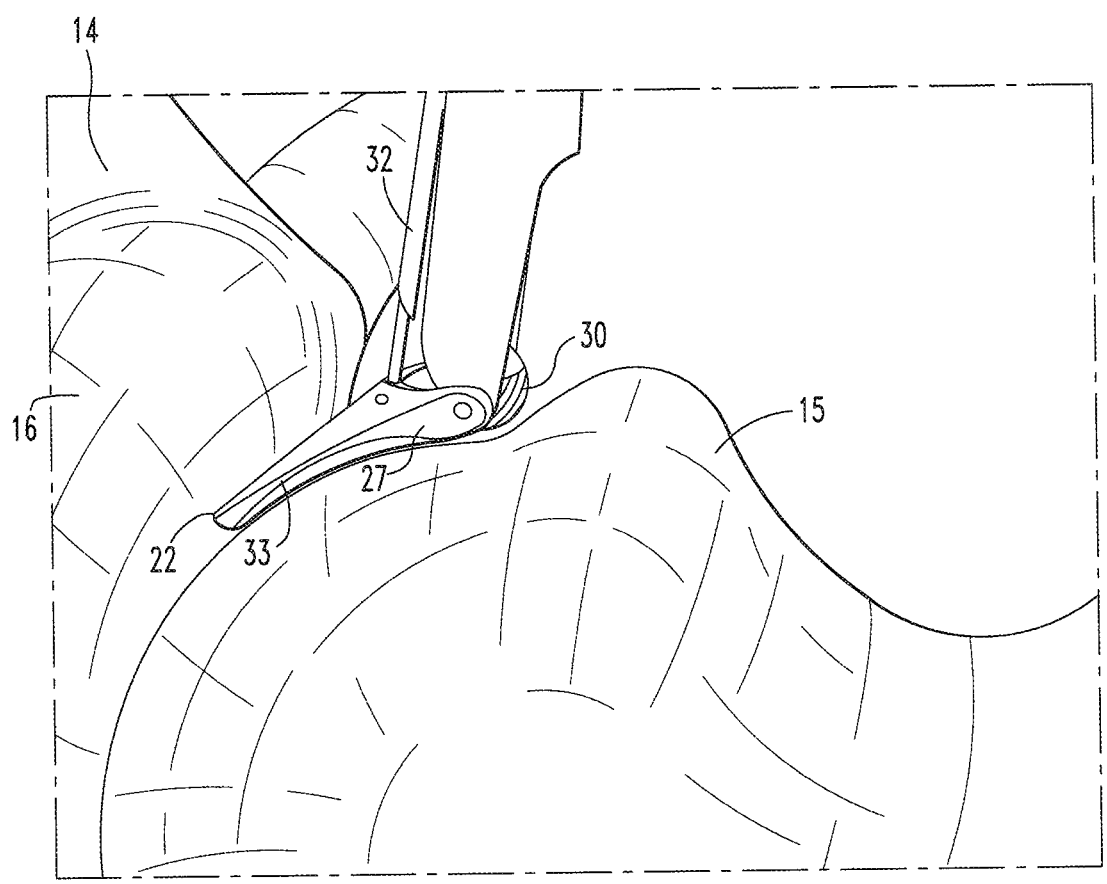
FIG. 3 is an isometric view of the embodiment of FIG. 2.

In FIGS. 2 and 3 there is shown a partial schematic view of a surgical instrument 20 in accordance with one embodiment of the present invention. The instrument 20 comprises a shaft 21, only the distal end of which is shown for clarity. The shaft 21 includes a template 22 pivotally connected thereto through pivot 23. The template 22 has a generally curved profile, having a lower concave region and an upper convex region, according to the illustration, in which the curvature of the lower concave region broadly matches the curvature of the femoral head 13. This curvature allows the template 22 to be mapped over the tissue surface and, where any deviations identified in any gaps between the curved lower surface of the template and the tissue surfaces, helps to highlight any changes in the curvature of the femoral head.

In alternative embodiments, not shown, the template does not have a generally curved profile. Instead, the template includes at least two tissue engaging regions or surfaces.

The template is suitably dimensioned to allow it to fit between the femoral head and acetabulum without it being necessary to distract the hip joint. Having said this, in some cases the hip may still be distracted or partially distracted to enable greater access to the joint.

The surgical instrument is available in a variety of different sizes so that an appropriately-sized instrument can be selected to suit the particular characteristics of a patient's acetabulofemoral joint. In alternative embodiments, not shown, the template may be appropriately-shaped to provide a template for a different joint such as, for example, the ankle.

Template 22 includes distal and proximal ends, 24 and 25 respectively, either or both of which may incorporate one or more bearings (not shown). In use, these bearings enable the template 22 to move more easily over the tissue surface, in this particular case the femoral head.

In addition, the instrument 20 also includes biasing means in the form of rod 32, pivotally attached about pivot 28 proximally to the template. Rod 32 is linked to the instrument handle, and is used to bias the template distally and towards a tissue surface over which it will be used. In embodiments in which the biasing means is a rod, the rod may include a spring or dampener 33, as shown. Rod 32 may be fixed at, or in the region of, the proximal end of template 22, thus inducing rotation of the template about the pivot 23.

In preferred embodiments, the template is only permitted to pivot within a single plane and so only a single rod is necessary to control and manipulate the template. However, in alternative embodiments (not shown) the template and shaft may be articulated in more than one plane. For example, the pivot may be a universal joint or a ball and socket joint. Such arrangements preferably require a pair of rods or wires as deployment means. In embodiments where the pivot is a universal joint or a ball and socket joint, the instrument may also include a lock to restrict motion of the joint to a single plane.

In alternative embodiments, (FIGS. 8-8B, below), the biasing means is a spring, or hinge 34 which is biased to extend the template distally.

The instrument 20 also incorporates a resecting means in the form of a burr. The burr includes a burr shaft (FIGS. 4 and 5, reference 29) and a generally spherical burr-head 30 which is designed to shave and/or resect the cartilage covering the femoral head, and any underlying bone protrusion, when the template is moved in a generally distal to proximal manner. The burr-head 30 is located at the distal end of burr, adjacent to the heal 27 of the template, or just proximally thereof, so that shaving or resection of tissue only occurs with notable changes in the curvature of the femoral head, and not when relatively minor differences are encountered by the template. As can be seen, as the instrument 20 is moved in a generally distal to proximal direction, burr-head 30 will engage the cartilage which covers a bump and/or the underlying bone, causing it to shave or resect the cartilage and bone in that region.

In alternative embodiments, not shown, the burr-head is located at the distal end of burr, intermediate the proximal and distal ends of the template.

In preferred embodiments, the pivotal connection 23 between the template 22 and burr is aligned with the centre of the burr-head 30. Accordingly, the curved tissue-engaging surface of the template 22 and the surface of the burr-head 30 are substantially tangential. The substantially tangential arrangement between the template and burr-head may be offset slightly deeper or shallower to account for cartilage compressibility. In addition, the burr includes a piston or dampener 50 and may also include centring means—all of which help to maintain the tangential arrangement between the template and burr-head as their relative positioning changes during movement of the instrument over a tissue surface. The burr or piston allows the burr-shaft 29 to move in an axial direction, indicated by arrow C, to offset changes in the compressibility of cartilage tissue and to also minimise any effects to the relative positioning of the burr-head and template as a result of movement of the instrument shaft 21, indicated by arrow. D. Whereas the centring means help to maintain the orientation of the burr-head relative to the template.

Figure 4:
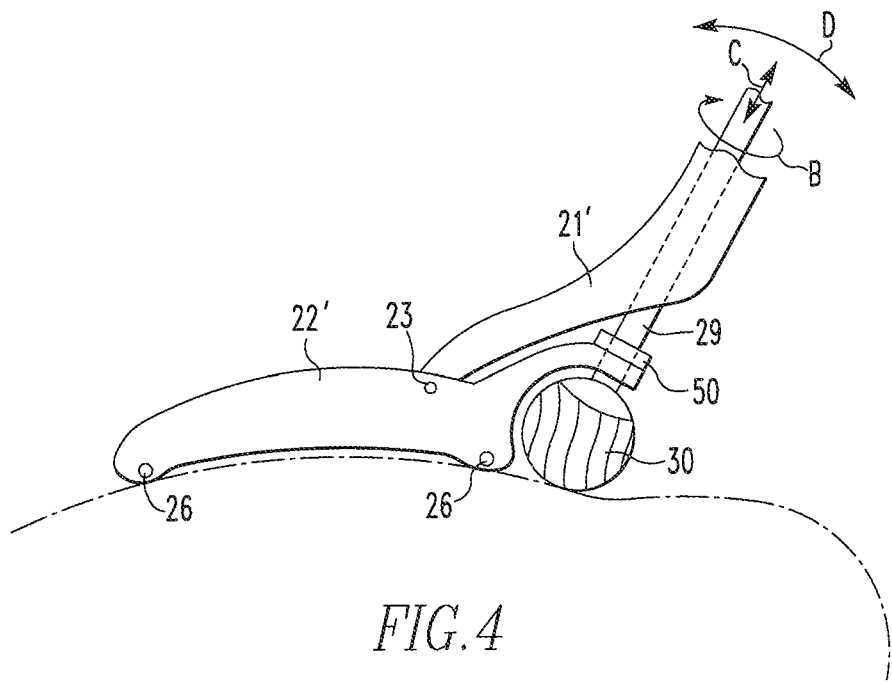
FIG. 4 is a schematic side-view of a second embodiment of an instrument according to the invention.
Figure 5:
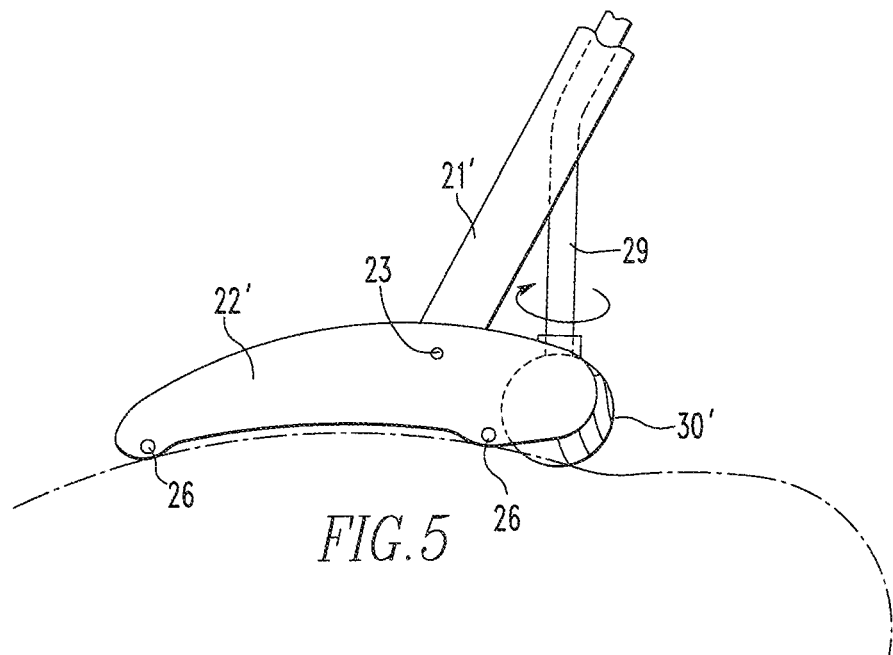
FIG. 5 is a schematic side-view of a third embodiment of an instrument according to the invention.

As shown more clearly in the embodiments of FIGS. 4 and 5, burr-head 30 is mounted at the distal end of a burr-shaft 29 which is disposed for rotation within shaft 21. The burr-shaft 29 may be straight, as depicted in FIG. 4, or at least in part curved, as depicted in FIG. 5. According to this construction, part of the burr-shaft, towards its distal end is curved, and the proximal end of the burr-shaft is coaxial with, and rotatable within, the shaft of the instrument. These embodiments do not require separate biasing means as the force through shaft 21 is distributed between bearings 26 and acts to push the template against the tissue surface, and so the shaft is the biasing means.

The burr-shaft may be solid or hollow. In preferred embodiments, the shaft 21 is hollow and includes an aperture between it and burr-shaft 29, substantially adjacent to the proximal end of burr, which allows resected tissue to be removed from the surgical site. In further preferred embodiments, the burr is formed with a separate shank (not shown) that is mounted to the burr-shaft. In such further preferred embodiments, the aperture which allows fluid communication with the hollow burr-shaft, is also formed in the shank. According to this construction, the shank, incorporating the burr and aperture, is formed from hardened steel, and is subsequently coupled with the hollow burr-shaft by a suitable manufacturing process, such as by swaging or welding.

This construction is advantageous because of the strength it provides in the region of the join with the burr, which also allows the distance between the aperture and the burr to be reduced. That is to say, providing a shank with an aperture allows the aperture to be located much closer to the burr, without compromising the overall strength and durability of the device.

In alternative embodiments, not shown, the resecting means is a radio frequency electrode, or the combination of a radio frequency electrode and a burr. In such embodiments, the lower concave region of the template may be designed with a recess, or so that the concavity is not uniform in order to accommodate the electrode. This allows the electrode to be fitted to the template, leaving a small amount of clearance between the template and femoral head when the template is mapped over regions of 'normal' curvature. When such a template encounters a bump, the electrode comes into contact with the bump and may be automatically activated to mark it as a result of the contact between the electrode and bump. In this manner, the instrument can be used to accurately mark the perimeter of a bump. In alternative embodiments, the electrode may be activated manually by the surgeon who will energise the electrode by pressing a button on the instrument handle or foot pedal. The advantage of this arrangement is that the surgeon can selectively mark the bump, moving the instrument over the site a number of times, and not marking it until they are satisfied that they have correctly identified a bump, so that he or she can be sure of the region being marked.

The surgical instrument also includes control means (not shown) for controlling the resecting means. The control means provide selective activation and deactivation of the resecting means which helps to reduce the amount of unnecessary damage within the surgical site. This also allows the surgeon to identify and check any differences in the curvature of the femoral head with the template before deciding to resect the tissue. Typically, the surgeon will activate the resecting means by pressing a button on the instrument handle or foot pedal. The advantage of this arrangement is that the surgeon can selectively resect the bump, moving the instrument over the site a number of times, and not activating the resecting means until they are satisfied that they have correctly identified a bump.

A particular advantage of this instrument is that the integral resecting means shortens the procedure by removing the intermediate step of marking the cartilage or bone tissue prior to its resection. This helps to reduce the amount of time spent in the joint and thus any associated trauma, and may help to speed up recovery times.

Figure 6:
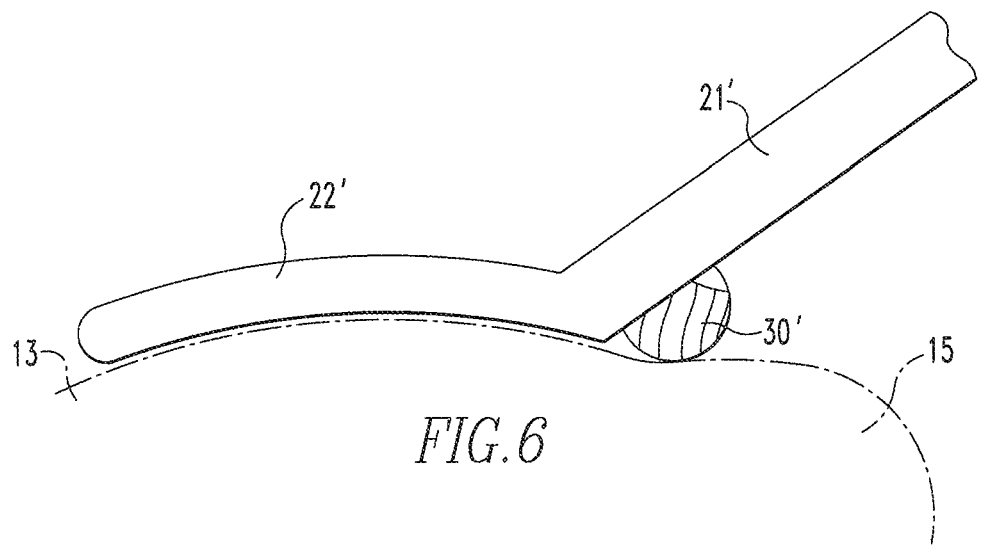
FIG. 6 is a schematic side view of a fourth embodiment of an instrument according to the invention.
Figure 7:
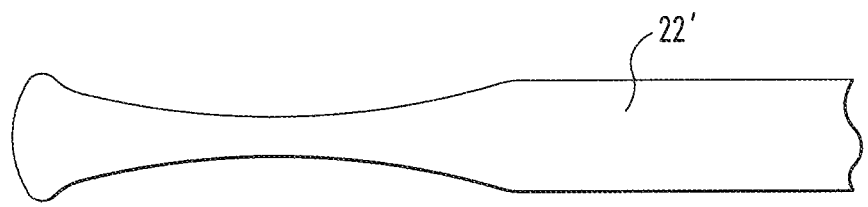
FIG. 7 is a partial top-plan view of the instrument of FIG. 6.

As shown in FIGS. 6 and 7, in further alternative embodiments, the template is connected with and is substantially rigid relative to the shaft. In these embodiments, the substantially spherical shape of the template is incorporated in the side edges of the template, so that the template is utilised with the template in a side-on orientation (FIG. 6). In this case, rotating the shaft of the surgical instrument allows the template to roll relative to the tissue surface. This is different to the sliding action utilised in the other described embodiments. The resecting means or burr is also wrapped around the edges of the template so that it may engage with tissue regardless of orientation.

Figure 8:
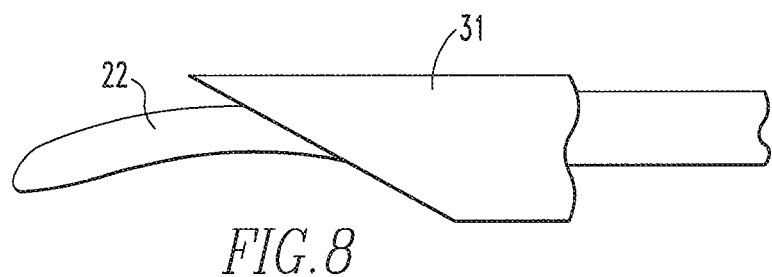
FIGS. 8-8B are schematic partial side-views of an instrument of according to the invention including an external obturator.
Figure 8A:
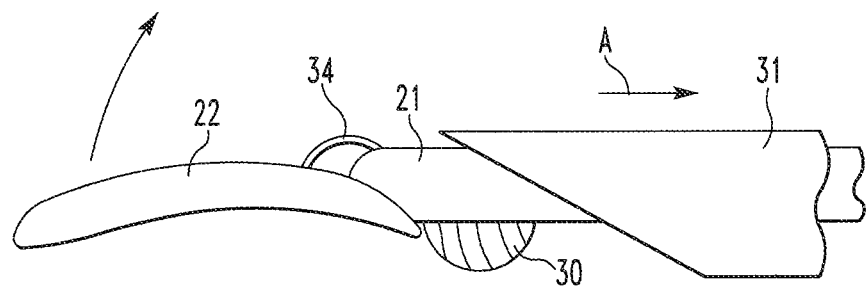
Figure 8B:
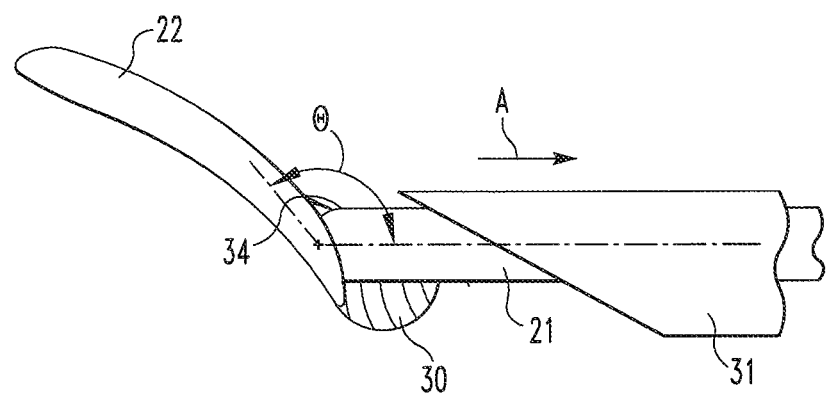

In the embodiments shown schematically in FIGS. 8-8B, shaft 21 is partly surrounded by an obturator in the form of a retractable outer sheath 31. The obturator is a tubular member coaxially mounted with the shaft which supports and protects the template whilst the instrument is packaged and/or when the instrument is being introduced into a surgical site. Outer sheath 31 includes an opening at a distal end and can be moved in an axial direction (represented by arrow A), and is shown in greater detail in FIGS. 8A and 8B, in which outer sheath 31 has been retracted towards a proximal handle (not shown). In FIG. 8, the template is shown in a retracted or stowed position in which it partly fits within outer sheath 31. The provision of an outer sheath allows the surgical instrument 20 to be passed down a cannula and into a surgical site with, relative ease. In practice, as outer sheath 31 is retracted, the template will pivot to a deployed position illustrated in FIG. 8B as a result of the inherent tension provided by biasing means 34.

The outer sheath 31 may be advanced and retracted by means of complementary axial threads on the outer surface of the shaft and inner surface of outer sheath. Alternatively, the outer sheath may be slid up and down the shaft, or may include a combination of both—for example, it may be advanced and retracted in a sliding manner that incorporates a twisting or screwing action at or towards the extreme ends of its desired motion in order to lock the sheath in position.

In the fully deployed position shown in FIG. 8B, the angle θ between the template and the shaft, and thus the operating range, is between around 5 degrees and 100 degrees.

In alternative embodiments, not shown, the instrument includes an internal obturator for supporting and protecting the template whilst the instrument is packaged for storage or whilst it is being introduced into a joint. The internal obturator may be a solid rod or a hollow tube.

The obturator may be slidably or rotatably attached to the instrument, or may be removable.

In use, the obturator fixes the template in a stowed position, in which it is aligned substantially with the longitudinal axis of the shaft. Once the instrument has been passed through a cannula and into the surgical site of a joint, the obturator may be removed, or retracted, or the biasing means suitably manipulated, to deploy the template into an operational position. The instrument can then be used to mark or resect any differences in the curvature of a tissue surface which are deemed to impede movement of the joint. At the end of the procedure, prior to removal of the instrument from the surgical site, the obturator may be advanced distally, relative to the shaft, or the biasing means manipulated accordingly, to substantially realign the template with the longitudinal axis of the shaft, and place it in the stowed position. The instrument is then withdrawn.

The surgical instrument also includes a lock (not shown) to prevent the obturator from impeding movement of the template when in a deployed position, and for locking the instrument in the template-stowed position for transit. The lock may be any suitable locking means, such as a twist-lock, button or catch.

Figure 9:
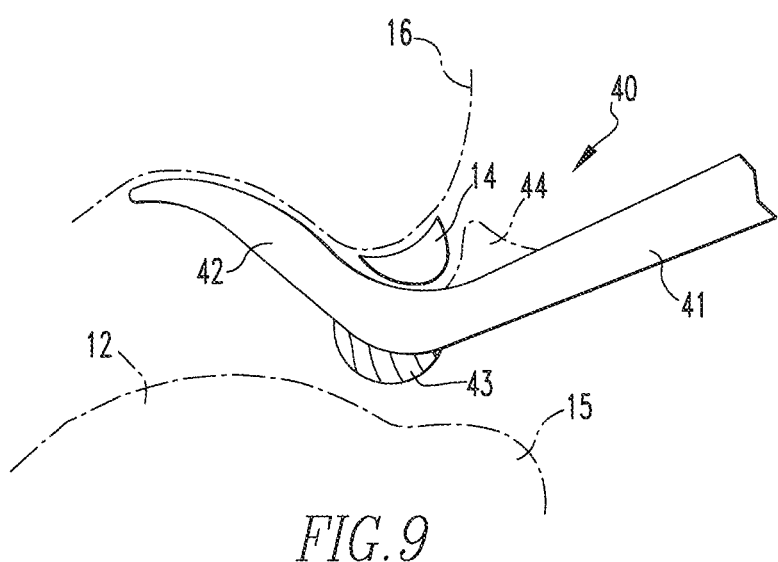
FIG. 9 is a side-view of a fifth embodiment of an instrument according to the invention.

In FIG. 9 there is shown an embodiment alternative instrument 40 including a shaft 41 and template 42. The template 42 is pivotally mounted to the shaft 41 about a pivot (omitted for clarity) and includes resecting means in the form of burr 43. In use, instrument 40 utilises the acetabular surface corresponding to the femoral head to guide the template, rather than the femoral head itself. In an analogous manner to that described above in relation to other embodiments, removal of the bump is carried out by moving the instrument distally to proximally. Accordingly, the distal upper surface of the template is engaged with the concave inner surface of the acetabulum, and the proximal lower surface of the template with the femoral head. As the instrument is moved in the distal to proximal direction, the template moves over the respective surfaces of the acetabulum and femoral head. However, when the portion of the template which is engaged with the femoral head encounters a difference in the curvature, in the form of a bump, burr 43 engages with the bump causing the tissue to be resected.

The instrument may also include suitable biasing means as described above:

Instrument 40 may optionally also include an acetabular rim stop 44 (shown in hashed lines). The rim stop 44, acts to prevent the instrument from being inserted too deeply into the acetabulofemoral joint and aids the correct alignment of the template burr.

As not all joints are spherical, these concepts may be used to extend to substantially non-spherical joints, such as the ankle joint which is more cylindrical than spherical.

The clinical technique of all embodiments concerning the first aspect of the invention does not require for the joint to be fully distracted due to the arm of the instrument being suitably dimensioned to slip unimpeded between the femoral head without distraction, where the joint being investigated and treated is the hip. However, it may be desirable to partly distract the joint enough to allow the template of the surgical instrument to have greater access to the joint.

The described arthroscopic approaches could provide considerable advantages over traditional, open surgery, methods. In particular, these instruments and techniques could lead to a quicker rehabilitation with less chance for iatrogenic damage when dislocating the joint.

The integral resecting means eliminates the intermediate step of marking the cartilage before resecting.

Although specifically described in the context of the femoral head, it will be recognised that the instrument could be used in other suitable joints such as the ankle.

The invention claimed is:

1. A surgical instrument, comprising:
    a shaft having a proximal end, a distal end, and a longitudinal axis extending therebetween;
    a handle disposed towards the proximal end of the shaft;
    a template pivotally connected towards the distal end of the shaft, the template having:
        a proximal end, a distal end, and a heel portion disposed at the proximal end of the template;
        first and second opposing surfaces positioned between the proximal and distal ends and dimensioned to fit between first and second bones of a joint; and
    a burr for removing tissue, the burr being coupled to the proximal end of the template and positioned to face the second bone of the joint when positioned between the first and second bones of the joint, the burr configured to rotate about an axis of rotation that is parallel to the longitudinal axis of the shaft, wherein the burr has a predetermined orientation relative to the template,
    wherein the second surface of the template has a concave shape to complement a curvature of the second bone of the joint, and wherein the second surface of the template is operative to engage with a surface of the second bone whereby the burr is operative to only engage and remove material from portions of the second bone having a surface curvature deviating from a curved path defined by the template while the second surface of the template guides movement in at least a distal to proximal manner over the second bone surface.

2. An instrument as claimed in claim 1, wherein the template is pivotally connected at or towards the proximal end of the template or between the proximal and distal ends of the template.

3. An instrument as claimed in claim 2, wherein the pivotal connection allows the template to pivot within a single plane.

4. An instrument as claimed in claim 2, wherein the pivotal connection comprises a universal joint or a ball-and-socket joint.

5. An instrument as claimed in claim 4, wherein the pivotal connection comprises a lock to restrict motion of the joint to a single plane.

6. An instrument as claimed in claim 1, wherein the template is connected to the distal end of the shaft by a resiliently flexible member.

7. An instrument as claimed in claim 6, wherein the resiliently flexible member is configured to bias the template towards a tissue surface.

8. An instrument as claimed in claim 7, wherein the resiliently flexible member comprises a Nitinol wire, a Nitinol tube, a spring, a live-hinge or a corrugated portion.

9. An instrument as claimed in claim 1, wherein the template is connected with and is rigid relative to the shaft.

10. An instrument as claimed in claim 1, wherein the burr comprises a generally spherical burr-head mounted on, or formed integrally with, a burr-shaft.

11. An instrument as claimed in claim 10, wherein the burr-shaft is mounted coaxially with, and rotatable within, the instrument shaft.

12. An instrument as claimed in claim 10, wherein the burr-shaft is in part mounted coaxially with, and rotatable within, the instrument shaft.

13. An instrument as claimed in claim 12, wherein the predetermined orientation of the burr relative to the template is determined by the connection between the template and shaft, the connection being aligned with the centre of the burr-head.

14. An instrument as claimed in claim 13, wherein the concave surface of the template and a surface of the burr-head are tangential.

15. An instrument as claimed in claim 14, wherein the tangential arrangement between the template and burr-head may be offset slightly deeper or shallower to account for tissue compressibility.

16. An instrument as claimed in claim 15, wherein the burr-shaft includes a piston or dampener.

17. An instrument as claimed in claim 16, wherein the burr-shaft includes a centering means to maintain a tangential arrangement between the template and the burr-head during movement of the instrument over a tissue surface.

18. An instrument as claimed in claim 1, wherein the surgical instrument comprises control means for the burr.

19. An instrument as claimed in claim 1, wherein the instrument comprises biasing means to bias the template towards a tissue surface.

20. An instrument as claimed in claim 19, wherein the biasing means is the instrument shaft, or a separate rod, spring, live-hinge or dampener which is biased to extend the template distally.

21. An instrument as claimed in claim 1, wherein the instrument comprises an obturator for supporting and protecting the template whilst the instrument is packaged and/or when the instrument is being introduced into a surgical site.

22. An instrument as claimed in claim 21, wherein the obturator comprises a solid cylindrical member or a hollow tubular member.

23. An instrument as claimed in claim 22, wherein the obturator comprises a tubular member coaxially mounted with the shaft and includes an opening at a distal end.

24. An instrument as claimed in claim 22, wherein the obturator is internally mounted within the shaft, or is an outer sheath mounted on an outer surface of the shaft.

25. An instrument as claimed in claim 24, wherein the obturator is slidably mounted or rotatably mounted on or within the instrument shaft.

26. An instrument as claimed in claim 25 wherein the obturator is removable.

27. An instrument as claimed in claim 26, wherein the surgical instrument includes a lock.

28. An instrument as claimed in claim 1, wherein the template further comprises one or more bearings which assist movement of the template over a tissue surface.

29. An instrument as claimed in claim 28, wherein the template comprises two, three, four, five or six bearings.

30. An instrument as claimed in claim 1, wherein the template is dimensioned for receipt between the two bones of the joint without distraction of the joint.

31. An instrument as claimed in claim 1, wherein the second bone of the joint is a femur and the second surface has a concave shape to complement curvature of a head of the femur.

32. An instrument as claimed in claim 1, wherein the first bone of the joint is hip bone and the first surface has a convex shape to complement curvature of an acetabular cavity of the hip bone.

33. The instrument as claimed in claim 1, wherein the curved path defined by the template is defined by a curvature of the second surface of the template.

34. The instrument as claimed in claim 1, wherein a cutting surface of the burr is substantially aligned with a curvature of the second surface of the template.

35. The instrument as claimed in claim 1, wherein at least a portion of the burr extends proximally relative to the heel portion of the template.

36. The instrument as claimed in claim 1, wherein the burr is closer to the proximal end of the template than the distal end of the template.

37. The instrument as claimed in claim 1, wherein the burr is the only resecting means in the instrument.

38. The instrument as claimed in claim 1, wherein the burr is partially enclosed by the heel portion.

39. A surgical instrument, comprising:
- a shaft having a proximal end, a distal end, and a longitudinal axis extending therebetween;
- a handle disposed towards the proximal end of the shaft;
- a template pivotally connected towards the distal end of the shaft, the template having:
  - a proximal end, a distal end, and a heel portion disposed at the proximal end of the template;
  - first and second opposing surfaces positioned between the proximal and distal ends and dimensioned to fit between first and second bones of a joint; and
- a burr for removing tissue, the burr being coupled to the proximal end of the template and open to the second surface, the burr configured to rotate about an axis of rotation that is parallel to the longitudinal axis of the shaft, wherein the burr has a predetermined orientation relative to the template,
- wherein the first surface of the template has a convex shape to complement curvature of the first bone of the joint;
- wherein the first surface of the template is operative to engage with a surface of the first bone whereby the burr is operative to only engage and remove material from the second bone having a surface curvature deviating from a curved path defined by the template while the first surface of the template guides movement of the template in at least a distal to proximal manner over the first bone surface.

40. An instrument as claimed in claim 39, wherein the second surface of the template has a concave shape to complement curvature of a portion of the second bone of the joint, wherein a proximal portion of the second surface of the template is operative to engage with a surface of the second bone while a distal portion of the first surface of the template engages with the first bone, and wherein the first and second surfaces of the template cooperate to guide the movement of the template in the at least distal to proximal manner over the first and second bone surfaces.

41. An instrument as claimed in claim 39, wherein the first bone of the joint is hip bone and the first surface has a convex shape to complement curvature of an acetabular cavity of the hip bone.

42. The instrument as claimed in claim 39, wherein the burr is partially enclosed by the heel portion.

* * * * *